United States Patent
Ward

(10) Patent No.: US 7,439,337 B2
(45) Date of Patent: Oct. 21, 2008

(54) THREE-PHASE PARTITIONING METHOD FOR PURIFYING A PROTEIN

(75) Inventor: William W. Ward, Metuchen, NJ (US)

(73) Assignee: Rutgers, the State University of New Jersey, New Brunswick, NJ (US)

( * ) Notice: Subject to any disclaimer, the term of this patent is extended or adjusted under 35 U.S.C. 154(b) by 0 days.

(21) Appl. No.: 11/832,830

(22) Filed: Aug. 2, 2007

(65) Prior Publication Data

US 2008/0033152 A1    Feb. 7, 2008

Related U.S. Application Data

(60) Provisional application No. 60/821,164, filed on Aug. 2, 2006.

(51) Int. Cl.
*A23J 1/00*    (2006.01)
(52) U.S. Cl. ...................................................... 530/412
(58) Field of Classification Search ....................... None
See application file for complete search history.

(56) References Cited

OTHER PUBLICATIONS

Sharma et al., "Purification of alkaline phospatase from chicken intestine by three-phase partitioning and use of phenyl-Sepharose 6B in the batch mode," Bioseparation 9, 2000, pp. 155-161.*
Keilin et al., "Purification of Horse-Radish Peroxidase and Comparison of its Properties with those of Catalase and Methaemoglobin", J. Biochem. 1951 49:88-104.
Kenten et al., "A Simple Method for the Preparation of Horseradish Peroxidase", J. Biochem. 1954 57:347-348.
Shannon et al., "Peroxidase Isozymes from Horseradish Roots", J. Biol. Chem. 1966 241(9):2166-2171.

* cited by examiner

*Primary Examiner*—Kathleen Kerr Bragdon
*Assistant Examiner*—Agnes B. Rooke
(74) *Attorney, Agent, or Firm*—Licata & Tyrrell P.C.

(57) ABSTRACT

The present invention is a kit and method for purifying a protein of interest.

6 Claims, No Drawings

THREE-PHASE PARTITIONING METHOD FOR PURIFYING A PROTEIN

INTRODUCTION

This application claims benefit of U.S. Provisional Patent Application Ser. No. 60/821,164, filed Aug. 2, 2006, the content of which is incorporated herein by reference in its entirety.

BACKGROUND OF THE INVENTION

There is a growing need in the biotechnology, biopharmaceutical, and research fields for a fast, efficient, versatile, and inexpensive low volume, one-step, micro-scale method, in kit form, to prepare small quantities of proteins for early-stage exploratory research. To move forward with early-stage exploratory research, it is essential to be able to quantitate the levels of the proteins of interest and to remove substances that might interfere with the properties and functions of these proteins. Protein quantitation is often accomplished via in vitro quantitative assays such as those employing optical detection methods. Such assay methods include, but are not limited to, colorimetry, fluorimetry, spectrophotometry, microtitre plate scanning, and optical microfluidics. Each of these optical assay methods suffers greatly in accuracy, producing falsely high and, on occasion, falsely low signals, if the sample in question contains unwanted, optically absorptive contaminants or if the sample is cloudy or turbid. Specific interference may occur, on a case-by-case basis, from substances that chemically react with assay reagents or that inhibit development of the assay in some fashion, as in the case of enzyme inhibitors. Thus, for accurate quantification of the protein of interest, removal of such contaminants is essential.

A single, low-volume, micro-scale, one-step method (in kit form) for wholesale contaminant reduction would be highly desirable. If applicable to a large variety of proteins from many different sources, the method would be even more desirable. Furthermore, a kit-based method that is versatile, fast, efficient, and cost-effective is even more desirable. Lastly, if that method is fully scaleable, it could have significant applications in large-scale commercial protein production. Thus, if the same micro-scale method used as a kit to pre-screen proteins were to be almost infinitely scaleable (while remaining fast, efficient, versatile, and inexpensive), then it could be applied, economically and effectively, to large-scale protein production and manufacturing. Outstanding benefits would accrue if the same one-step method could achieve, on both the micro-scale and the macro-scale, very significant reductions in levels of DNA, cell debris and other particulates, lipids, water-soluble and water-insoluble pigments and other small molecules, and many extraneous, contaminating proteins. Further benefits could arise if the same method were to greatly lower viscosity while greatly reducing total sample volume.

Such needs are especially relevant for naturally occurring proteins that have neither been cloned nor genetically engineered to contain an affinity ligand that facilitates rapid protein purification by affinity chromatography or affinity trapping methods. While cloning and affinity tagging a protein is often the method of choice for late-stage protein research, development, and manufacturing, cloning and affinity tagging is not always cost-effective or time-efficient for very early-stage proteins that are more likely than not to fail in early trials. It is much more cost-effective to perform early trials on proteins extracted from natural sources. But, as proteins from natural sources have no affinity tags, extraction, purification, viscosity reduction, particulate removal, and contaminant reduction often require multiple, tedious, and time-consuming steps. A one-step procedure for naturally occurring proteins (equivalent in many respects to affinity methods for cloned proteins) would be highly desirable. Furthermore, even in cases where a protein has succeeded in early trials and has been cloned and affinity tagged, that protein must be extracted from cells in a cost-effective way and must be prepared for affinity chromatography in ways that facilitate effective separation of the protein of interest while preserving the resolving power and the lifetime of the affinity adsorbent—often a very expensive material. Usually, such pre-column preparations involve multiple, independent steps beginning with non-selective extraction of all water-soluble components of the cells by cell lysis methods such as sonication, homogenization, freeze-thaw lysis, lysozyme treatment, bead mills, French press, or organic solvent treatment. Following extraction, it may be necessary, so as to effect resolving power of the affinity column and to increase column lifespan, to separate out particulates, to lower viscosity by removing DNA, polysaccharides, and lipid micelles, and to effect buffer exchange to facilitate proper affinity binding conditions and/or prevent precipitation of contaminants during affinity chromatography. In the case of immobilized metal affinity chromatography (IMAC), the HIS6-tagged recombinant protein cannot be successfully trapped by the immobilized metal ion without prior removal of other chelators such as citrate, ammonia, and EDTA. Thus a buffer exchange is often required to remove such materials and to create a slightly alkaline pH environment.

Examples of naturally occurring proteins for which a cost-effective and time-efficient purification method is needed include peroxidases, antibodies, fluorescent proteins such as GFP, and other proteins commonly employed in research, diagnostics and therapeutics. For example, horseradish peroxidase (HRP), a protein of approximately 40 kDa, is one of the two most widely used enzyme labels in medical diagnostics and research applications, the other being alkaline phosphatase. Horseradish peroxidase is applied often in immunoassays and nucleic acid hybridization assays, in part because of the availability of peroxidase-conjugated antibodies to haptens such as biotin, fluorescein isothiocyanate, and digoxigenin.

Horseradish peroxidase has been isolated using various methods. For example, Shannon et al. ((1966) *J. Biol. Chem.* 241:2166) teach ammonium sulfate fractionation followed by CM-cellulose and DEAE-cellulose chromatography. Keilin and Hartree ((1951) *Biochem. J.* 49:88) teach ammonium sulfate fractionation, precipitation with ethanol, fractionation with calcium phosphate and ethanol, and fractionation with ammonium sulfate. Kenten and Mann ((1954) *J. Biochem.* 57:347-348) disclose purification of horseradish peroxidase by ethanol:chloroform extraction followed by ammonium sulfate fractionation and ethanol precipitation.

However, there is a need in the art for improved methods for high yield purification of proteins and enzymes. The present invention meets this need in the art.

SUMMARY OF THE INVENTION

The present invention is a kit for purifying a protein of interest. The kit includes a 2.4 M solution of ammonium sulfate containing an indicator dye; and a solution of tertiary butanol and isopropanol at a ratio of 3:7. In some embodiments, the kit further includes a protein purification matrix. A method for using the kit of the invention is also provided.

DETAILED DESCRIPTION OF THE INVENTION

A novel kit-based application for three-phase partitioning (TPP) has now been developed for use in protein purification. Wherein conventional TPP employs one volume of 1.6 M ammonium sulfate in water combined with one volume of neet t-butanol, the instant kit provides a 2.4 M solution of ammonium sulfate containing an indicator dye in combination with an alcohol solution containing tertiary butanol and isopropanol at a ratio of 3:7.

This protein purification kit, in a mini-prep format, was used to effectively purify GFP, IgG, IgY, peroxidases, alkaline phosphatase, Protein A, Protein G, five out of five common proteases, cytochrome c, and a variety of other proteins including bovine serum albumin, alpha lactalbumin, vitamin B-12, carbonic anhydrase, ovalbumin, pancreatin, myoglobin, hemoglobin and catalase. Moreover, the protein purification kit was used with a variety of biological starting materials. For example, a 65% recovery of GFP was achieved, on average, when the GFP was "spiked" into crude extracts of each of the following materials: egg yolk, egg white, B. subtilis cells, spinach, corn meal, fish meal, whole yeast, whole milk, firefly lanterns, firefly bodies, E. coli cells, and pancake batter. Moreover, purification factors averaged more than 120-fold. A near-universal protein purification kit that selectively extracts proteins of interest from whole, unlysed bacterial cells (and other cells and tissues), while substantially purifying and concentrating the extracted protein, is a novel use for three-phase partitioning.

Thus, in accordance with the present invention, a protein of interest is purified by employing a kit containing the following materials:

1. An ammonium sulfate solution (e.g., 2.4 moles/liter in 50 mM Tris-HCl with 0.01% w/v of indicator dye as a meniscus indicator); and
2. An alcohol solution of tertiary butanol and isopropanol (3:7 volume to volume ratio).

In general, the kit includes containers holding the ammonium sulfate solution and alcohol solution. Depending on the need of the user, the kit can be provided for micro- or macro-scale purification of one or more proteins of interest. As such, the containers can supply milliliter to Liter amounts of the ammonium sulfate and alcohol solutions.

To facilitate use of the instant kit, said kit can further include an instruction manual for using the solutions for the purpose of purifying one or more proteins. For example, an instruction manual can specify the appropriate dilution (e.g., with water) of the ammonium sulfate solution for use in purifying particular proteins of interest. By way of illustration, the instruction manual can instruct the user of the kit to employ the 2.4 M solution of ammonium sulfate, undiluted, to optimally purify cytochrome c, or dilute the ammonium sulfate solution to 0.8 M for optimal purification of IgG or 1.6 M for optimal purification of GFP or horseradish peroxidase. Moreover, the instruction manual can specify the ratio of ammonium sulfate solution to alcohol solution for use in purifying a protein of interest. While particular embodiments embrace the use of the ammonium sulfate solution and alcohol solution at a 1:1 ratio, it is contemplated that other ratios may be desirable for particular types of samples or proteins of interest.

Proteins which can be purified in accordance with the present kit and method include enzymes as well as structural proteins. Moreover, the protein of interest can be isolated from a natural source or can be a recombinant protein or protein fragment expressed in a recombinant host cell. In this regard, a protein of interest of the present invention includes, but is not limited to, a marker protein (e.g., GFP, luciferase, etc.), an antibody, a cytokine, serpin, protease, kinase, phosphatase, ras-like GTPase, hydrolase, transcription factor, heat-shock transcription factor, DNA-binding protein, zinc-finger protein, leucine-zipper protein, growth factor, homeodomain protein, intracellular signal transduction modulator or effector, apoptosis-related factor, DNA synthesis factor, DNA repair factor, DNA recombination factor, cell-surface antigen, hepatitis C virus protease, HIV protease, steroid hormone receptor, a growth factor receptor, hormone receptor, neurotransmitter receptor, catecholamine receptor, amino acid derivative receptor, cytokine receptor, extracellular matrix receptor, or lectin, or a fragment of any one of the above.

As exemplified herein, the protein of interest can be isolated from a variety of natural, artificial or recombinant sources. In this regard, a sample in accordance with the present invention includes, but is not limited to, a cell (e.g., prokaryotic or eukaryotic including plant and animal cells), tissue, organ, bodily fluid (e.g., blood, serum, urine, sputum, seminal fluid) or whole organism. Moreover, a sample is intended to include a cell or tissue extract or supernatant (e.g., a cell or tissue maintained in culture).

The sample can be used as is, or centrifuged or ground using any conventional means including the use of a blender or food processor and filtered (e.g., through cheesecloth, stainless steel mesh, nylon screen, sand or diatomaceous earth). Moreover, the sample can be maintained in an aqueous solution (e.g., water or buffered solution) at or near pH 7.0, with certain embodiments embracing an alkaline pH of 7.0 to 12. In particular embodiments, the aqueous solution further contains one or more protease inhibitors (e.g., PMSF, aprotinin, or a protease cocktail), to preserve the integrity of the protein of interest.

Purification of a protein of interest is achieved by mixing the ammonium sulfate solution (diluted as appropriate for optimal purification of the protein of interest) and alcohol solution with a sample containing a protein of interest, and centrifuging the resulting mixture to separate the phases into layers (e.g., 20 minutes at 5,000 rpm). Advantageously, the instant kit and method employ an indicator dye such as rhodamine B, phenol red, fluorescein, COOMASSIE brilliant blue R, crystal violet, cresol green, xylene cyanole, safranin O, aniline red, neutral red, Janus green, thymol blue, bromophenol blue, fast green FCF, or methyl orange, which have all been shown to differentiate the various phases. In this regard, the indicator dye partitions almost entirely into the upper mixed alcohol layer, containing cellular lipids including membrane components, such that this layer is readily identifiable. In contrast, the lower aqueous ammonium sulfate layer, which contains the protein of interest, appears as a clear solution, devoid of indicator dye. Thus, the three phases from bottom to top are: 1) an aqueous ammonium sulfate layer with soluble protein of interest, 2) insoluble solids that form a tight, rubbery disk at the meniscus (boundary layer), and 3) a mixed alcohol phase containing the readily visible indicator dye that overlays the boundary layer of insoluble solids. TPP-induced migration of the indicator dye from the ammonium sulfate solution to the alcohol solution, with the greatly enhanced concomitant color and/or fluorescence of the dye, provides a visual measure of confidence that TPP is working as described (quality assurance) and it makes removal of the upper layer (e.g., by aspiration), in preparation for the next step(s), easier to follow visually (by color and/or fluorescence).

As will be appreciated by the skilled artisan, the lower aqueous layer containing the protein of interest can be collected and subjected to further extraction to ensure removal of contaminants. For example, an equal volume of fresh alcohol solution can be added to the collected lower aqueous layer to cause the protein of interest to precipitate for the first time. Subsequent centrifugation produces a thin "skin" of insoluble, interstitial material within which the protein of interest is greatly enriched. This thin layer of insoluble material is then collected and dissolved in a minimal volume of the original ammonium sulfate solution. Upon subsequent centrifugation, insoluble contaminants are removed from the preparation containing the protein of interest.

For many applications, including rapid screening of expressed proteins in recombinant protein expression, the sample purity achieved by the modified TPP procedure of the instant invention may be sufficient. For other applications, greater purity may be desired to achieve a substantially purified preparation of the protein of interest, i.e., at least 80 to 99% pure or homogeneous to the protein of interest. Accordingly, the kit and the method of the invention further provide for the use of one or more protein purification matrices subsequent to purification with the ammonium sulfate and alcohol solutions. In this regard, the kit of the invention can optionally include one or more syringe-accessible single-use protein purification columns. Protein purification columns are well-known in the art and include, but are not limited, hydrophobic interaction, reverse-phase, and ion exchange matrices. It is contemplated that one or a combination of matrices can be employed. In particular embodiments, a substantially purified preparation of the protein of interest is obtained using a hydrophobic interaction matrix.

For the purposes of the present invention, any suitable hydrophobic interaction matrix can be employed for binding and eluting the protein of interest. Such hydrophobic interaction matrices include, but are not limited to, natural or artificial surfaces containing uncharged groups, such as methyl, ethyl, or other alkyl groups. These groups form hydrophobic bonds with proteins which are passed through the matrix and result in separation of proteins based on the strength of interaction between the protein and matrix groups. Hydrophobic interaction chromatography can be performed at low or high pressures, wherein the column is equilibrated in the presence of aqueous buffers using high salt concentrations (e.g., 1.2 to 1.7 M ammonium sulfate) and eluted in the presence of aqueous buffers using low salt concentrations (e.g., a decreasing ammonium sulfate gradient from 1.2 M to 0.5 M). As such, proteins are selectively eluted based on the differing strengths of hydrophobic interaction with the hydrophobic groups on the matrix, i.e., in order of increasing hydrophobicity of the protein. Examples of commercially available hydrophobic interaction matrices for low pressure applications include Pharmacia's phenyl-SEPHAROSE, and Tosohaas' butyl, phenyl and ether TOYOPEARL 650 series resins. An example of a syringe-accessible HIC column is the Phenyl SEPHAROSE High Trap column provided by GE Healthcare. Elution from the hydrophobic interaction matrix can be performed with a step-wise or linear gradient.

As indicated, the protein of interest can be applied to one or more ion exchange chromatography matrices to remove cationic and/or anionic contaminants. When applying the protein of interest to an anion exchange matrix any suitable matrix can be employed including, but not limited to aminoethyl, diethylaminoethyl, quaternary aminomethyl, quaternary aminoethyl, diethyl-(2-hydroxypropyl)aminoethyl, triethylaminomethyl, triethylaminopropyl and polyethyleneimine exchangers, to achieve filtration of the protein of interest. Examples of commercially available anionic exchangers include the cellulose ion exchangers such as DE32 and DE52 (WHATMAN, Florham Park, N.J.), the dextran ion exchangers such as DEAE-SEPHADEX C-25, QAE-SEPHADEX C-25, DEAE-SEPHADEX C-50 and QAE-SEPHADEX C-50 (Pharmacia, Piscataway, N.J.), the agarose or cross-linked agarose such as DEAE BIO-GEL A (BIO-RAD, Hercules, Calif.), DEAE-SEPHAROSE CL-6B and Q-SEPHAROSE Fast Flow (Pharmacia), the synthetic organic polymers, such as MONO Q (Pharmacia), DEAE-5-PW and HRLC MA7P (BIO-RAD) and the coated silica matrices such as DEAE Si5500 and TEAP Si100. Desirably, the anion exchange matrix is equilibrated in very low salt concentrations and employed at an alkaline pH (e.g., pH 8.0 to 11.5) to facilitate binding of acid and mildly basic contaminants.

When applying the protein of interest to a cation exchange matrix, it is contemplated that any matrix functionalized with carboxymethyl, sulfonate, sulfoethyl or sulfopropyl groups can be employed. Desirably, the cation exchange matrix is equilibrated and employed at an acidic pH (e.g., pH 3.0 to 6.5) to facilitate binding of basic and mildly acidic contaminants. Examples of commercially available cationic exchangers are the cellulose-based CM 23, CM 32 and CM 52 (WHATMAN); the dextran based CM-SEPHADEX C-25, SP-SEPHADEX C-25, CM-SEPHADEX C-50 and SP-SEPHADEX C-50 (Pharmacia); the agarose or cross-linked agarose-based CM BIO-GEL A (BIO-RAD), CM-SEPHAROSE Fast Flow and S-SEPHAROSE Fast Flow (Pharmacia); the synthetic organic polymer-based MONO S (Pharmacia), SP-5-PW and HRLC MA7C (BIO-RAD) and the coated silica matrices such as CM Si300 and SP Si100.

The support matrices for the chromatographic columns disclosed herein are not critical, however, support matrices based on dextran, cellulose, cross-linked agarose, synthetic organic polymers, coated silica or agarose are conventional in the art and suitable for use herein.

When employing a combination of separation matrices, e.g., hydrophobic interaction chromatography followed by ion exchange chromatography, it may be desirable to exchange the hydrophobic interaction elution buffer with a more suitable buffer for ion exchange chromatography. Moreover, depending on the volume of the original sample or purified sample and salts employed in the buffers, it may also be desirable to concentrate and desalt samples containing the protein of interest. Accordingly, the present invention further provides methods for concentrating, desalting and/or exchanging buffers. Such methods are conventionally employed in protein purification and, as such, the skilled artisan can readily apply the appropriate method depending on the intended result. For example, concentration and desalting can be carried out by standard methods such as rotaevaporation and direct flow membrane filtration (e.g., small-scale spin filters) or alternatively by employing tangential flow filtration (e.g., in large scale applications). To concentrate and desalt a sample by tangential flow filtration, a membrane is generally selected with a molecular weight cut off that is substantially lower than the molecular weight of the molecules to be retained. A general rule is to select a membrane with a molecular weight cut off that is 3 to 6 times lower than the molecular weight of the molecules to be retained. The membrane is installed, the tangential flow filtration system is initialized (typically flushed with water and tested for water filtrate flow rate and integrity), sample is added, a crossflow is established, feed and retentate pressures are set, and filtrate is collected. When the desired concentration or volume is reached, the process is stopped, and the sample is recovered.

The inclusion of a low molecular weight cut-off centrifugal ultra-filtration filter unit into the kit of the invention is also contemplated. Such a filter unit can be used to trap the protein of interest while exchanging the solvent prior to more extensive purification by ion exchange methods or gel electrophoresis. For larger scale applications, e.g., following successful trials with at the mini-prep level, buffer exchange can be achieved by diafiltration via tangential flow filtration. There are several ways to perform diafiltration. In continuous diafiltration, the diafiltration solution (water or buffer) is added to the sample feed reservoir at the same rate as filtrate is generated. In this way the volume in the sample reservoir remains constant, but the small molecules (e.g., salts) freely permeate through the membrane and are washed away. Using salt removal as an example, each additional diafiltration volume reduces the salt concentration further. In discontinuous diafiltration, the solution is first diluted and then concentrated back to the starting volume. This process is then repeated until the required concentration of small molecules (e.g., salts) remaining in the reservoir is reached. Each additional diafiltration volume reduces the salt concentration further.

Embodiments of the instant kit and method can provide a protein which is nearly homogeneous (i.e., >99% pure). As such, the proteins purified in accordance with the instant invention find application in a variety of diagnostic, therapeutic and research applications. Particular applications of the present invention include the purification of proteins which are useful to a variety of research purposes, e.g., fluorescent proteins such as GFP and enzymes such as horseradish peroxidase. Accordingly, when employed in the purification of GFP, referred to herein as "Green Gene Screen", particular embodiment embrace the inclusion of the following materials in the kit of the present invention:

1. A container or vial of pure, pre-calibrated recombinant GFP (as a calibration control);

2. A container or vial of freeze-dried, non-viable *E. coli* cells, (for practice); and 3. A 400 nm-emitting light source, e.g., a pen lite to excite GFP fluorescence and to enable the kit user to follow the fluorescence of GFP.

Given that horseradish peroxidase is a heme containing glycoprotein, phases containing horseradish peroxidase can be readily identified by visual means, e.g., by the naked eye or absorbance at 403 nm. Alternatively, the kit of the present invention can contain one or more common horseradish peroxidase substrates including, but not limited to, ABTS (2,2'-azino-di-(3-ethylbenzothiazoline-6-sulfonate)), OPD (o-phenylenediamine), TMB (3,3',5,5'-tetramethylbenzidine), or MBTH-DMAB (MBTH: 3-methyl-2-benzothiazoline hydrazone, DMAB: 3-(dimethylamino) benzoic acid) (Tijssen (1985) In: *Practice and Theory of Enzyme Immunoassays*, Burden and van Knippenberg, eds., Elsevier Science Publishers, Amsterdam The Netherlands). Moreover, using such reagents, purity and activity can be readily ascertained.

As will be appreciated by the skilled artisan, sample preparation throughout the disclosed method can include one or more centrifugation or filtration steps to remove particulate debris when present and can further include dilution, concentration, pH adjustment, or adjustment of salinity. For example, it may be necessary to adjust the pH of the sample so that the protein of interest will or will not bind to a particular chromatography matrix. Such sample preparations for chromatographic separation are well-known and within the means of those skilled in the art. See, e.g., Scopes, et al. (1994) In: *Protein Purification: Principles and Practice*, 3rd edition, Springer Verlag.

Advantageously, the instant method can be performed in a relatively short period of time, involves inexpensive reagents, and requires little sample preparation before and during the purification process. Thus, it is contemplated that the instant kit and method can be used in both micro- and macro-scale purification of proteins. Moreover, as application of three-phase partitioning removes most of the contaminants prior to hydrophobic interaction chromatography, the life of the hydrophobic interaction column can be extended with a reduction in the labor-intensive column cleaning and re-equilibration.

The invention is described in greater detail by the following, non-limiting examples.

EXAMPLE 1

Purification of GFP

When this less expensive, and more environmentally favorable TPP formulation was applied, in a mini-prep kit format, to an unlysed *E. coli* pellet of cells expressing GFP, followed immediately by hydrophobic interaction chromatography (HIC), >95% purity of GFP was routinely achieved with >80% overall recovery of GFP in a total elapsed time of 1-2 hours (Table 1).

TABLE 1

| | Vol. (mls) | Diln. | A257 | Total A257 | Diln. | Fluor. | GFP Std.* | mg GFP |
|---|---|---|---|---|---|---|---|---|
| Before TPP | 3 | 200 | 0.494 | 296 | — | 610 | 924 | 1.98 |
| After TPP | 4 | 1 | 0.266 | 2.13 | 50 | 739 | 924 | 1.60 |

Vol., Volume;
Diln., Dilution;
Fluor., Fluorescence;
Std. Standard;
*GFP standard was 5 µg/ml.

Thus, this modified TPP formulation selectively and quantitatively released, in 5 minutes, recombinant wild-type *Aequorea* GFP from whole, unlysed *E. coli* cells, and, in a 30-minute process removed virtually all chromosomal DNA, all lipids and lipid micelles, all cellular debris and other particulate material, all autofluorescence from extraneous cellular materials, and all small molecules including both water-soluble and water-insoluble pigments, while, simultaneously lowering absorbance at 280 nm by as much as 100-fold and decreasing solvent volume by as much as 50-fold. The post-TPP application of a single HIC step (e.g., using a GE Healthcare, syringe-accessible Phenyl SEPHAROSE High Trap column or the equivalent) removed all traces of organic solvent, removed nearly all remaining protein contaminants, and effected a buffer exchange.

Artificial samples such as corn meal, spinach, egg white, etc. were spiked with GFP. GFP was subsequently purified from these samples using the instant modified TPP method with the resulting purification listed in Table 2.

TABLE 2

| Source | Starting Total A280 | Recovered Total A280 | Recovered Total A397 | % Recovered GFP | Pfn Factor |
|---|---|---|---|---|---|
| Corn Meal | 140 | 3.19 | 0.218 | 57 | 25X |
| Yeast | 3720 | 9.34 | 0.187 | 49 | 195X |
| Rabbit Muscle | 532 | 13.2 | 0.178 | 47 | 19X |
| Firefly | 6552 | 7.34 | 0.312 | 82 | 732X |

TABLE 2-continued

| Source | Starting Total A280 | Recovered Total A280 | Recovered Total A397 | % Recovered GFP | Pfn Factor |
|---|---|---|---|---|---|
| Lanterns Firefly Body | 838 | 9.22 | 0.402 | 106 | 96X |
| Fish Meal | 1222 | 17.8 | 0.200 | 105 | 72X |
| Pancake Batter | 498 | 2.40 | 0.172 | 45 | 93X |
| Spinach | 288 | 2.67 | ~0.300 | ~80 | 86X |
| Egg Yolk | 444 | 11.7 | 0.248 | 65 | 25X |
| Egg White | 270 | 25.6 | 0.151 | 40 | 4.2X |
| Cabbage Looper | 114 | 14.5 | 0.270 | 71 | 55X |
| *B. subtilis* | 664 | 13 | 0.265 | 70 | 36X |
| Average | | | | 68% | 120X |

Pfn, Purification.

What is claimed is:

1. A protein purification kit comprising
   a M solution of ammonium sulfate containing an indicator dye, and
   a solution of tertiary butanol and isopropanol at a ratio of 3:7.

2. The protein purification kit of claim 1 wherein the indicator dye partitions into the organic phase and is selected from the group consisting of rhodamine B, phenol red, fluorescein, COOMASSIE brilliant blue R, crystal violet, cresol green, xylene cyanole, safranin O, aniline red, neutral red, Janus green, thymol blue, bromophenol blue, fast green FCF, or methyl orange.

3. The kit of claim 1, further comprising a protein purification matrix.

4. A method for purifying a protein of interest from a sample comprising
   a) mixing a sample containing a protein of interest with
      i) a solution of ammonium sulfate containing an indicator dye, and
      ii) a solution of tertiary butanol and isopropanol at a ratio of 3:7;
   b) separating the mixture of step a) to obtain a layer containing the protein of interest; and
   c) collecting the layer containing the protein of interest thereby purifying the protein of interest from the sample.

5. The method of claim 4 wherein the indicator dye partitions into the organic phase and is selected from the group consisting of rhodamine B, phenol red, fluorescein, COOMASSIE brilliant blue R, crystal violet, cresol green, xylene cyanole, safranin O, aniline red, neutral red, Janus green, thymol blue, bromophenol blue, fast green FCF, or methyl orange.

6. The method of claim 4, further comprising
   d) applying the collected protein of interest to a protein purification matrix; and
   e) eluting the protein of interest from the protein purification matrix thereby substantially purifying the protein of interest.

* * * * *